United States Patent [19]

Joy

[11] 4,166,733
[45] Sep. 4, 1979

[54] CACODYLIC ACID-MONOSODIUM ACID METHANEARSONATE HERBICIDE COMBINATION

[75] Inventor: Donald N. Joy, Yakima, Wash.

[73] Assignee: Crystal Chemical Company, Houston, Tex.

[21] Appl. No.: 945,783

[22] Filed: Sep. 25, 1978

Related U.S. Application Data

[63] Continuation of Ser. No. 645,450, Dec. 30, 1975, abandoned, which is a continuation of Ser. No. 829,711, Jun. 2, 1969, abandoned.

[51] Int. Cl.$^2$ .............................................. A01N 9/24
[52] U.S. Cl. ...................................................... 71/97
[58] Field of Search ........................................... 71/97

[56] References Cited
U.S. PATENT DOCUMENTS

| 2,678,265 | 5/1954 | Schwerdle | 71/97 |
| 3,056,668 | 10/1962 | Sprague | 71/97 |
| 3,076,699 | 2/1963 | Renner | 71/97 |
| 3,342,584 | 9/1967 | Harnden et al. | 71/97 |
| 3,466,163 | 9/1969 | Kirch | 71/97 |

OTHER PUBLICATIONS

Shephard et al., Proc. 19th Southern Weed Conference (1966), pp. 542–544.
Stevens, Proc. 19th Southern Weed Conference (1966), pp. 545–549.

Primary Examiner—Catherine L. Mills
Attorney, Agent, or Firm—Ned L. Conley; Murray Robinson; David Alan Rose

[57] ABSTRACT

This invention provides a process for the control of broadleaf weeds and grasses. The process comprises applying to an area containing broadleaf weeds and grasses a composition comprising a mixture of about 1 to 2 parts by weight of cacodylic acid or salts thereof and about 2 to 4 parts by weight of methane arsonic acid or salts thereof.

1 Claim, No Drawings

CACODYLIC ACID-MONOSODIUM ACID METHANEARSONATE HERBICIDE COMBINATION

CROSS REFERENCE TO RELATED APPLICATIONS

This application is a continuation of Application Ser. No. 645,450, filed Dec. 30, 1975 and now abandoned, which was in turn a continuation of Application Ser. No. 829,711, filed June 2, 1969 and now abandoned.

This invention relates to a process for the control of broadleaf weeds and grasses. More particularly, the invention relates to a herbicide combination for the wide control of a broad spectrum of broadleaf weeds and grasses.

Moreover, this invention relates to a process of controlling broadleaf weeds and grasses by the application of a composition comprising cacodylic acid or salts thereof and methane arsonic acid or salts thereof.

In the control of various weeds and grasses, it has been necessary to apply various individual herbicides to destroy or kill a wide range of unwanted weeds and grasses such as Pigweeds, Morning Glory, Japanese Millet and Johnsongrass. There are various herbicides which are effective for the control of specific and individual weed and grass species. However, these individual herbicides are limited in that they are not always effective in controlling both broadleaf weeds and grasses.

It is therefore an object of the present invention to provide a herbicide combination which alone will effectively control a broad spectrum of undesired broadleaf weeds and grasses.

Another object of this invention is to provide an economical way of controlling effectively the growth of undesired broadleaf weeds and grasses.

There have been various attempts to develop a combination of herbicides and materials which will effectively control the growth of broadleaf weeds and grasses, and at the same time not damage or impair the desired grasses and weeds.

In one attempt, there was provided for weed control a combination of sodium methyl arsonate and an inert diluent which was sufficient to destroy crabgrasses, and insufficient to destroy or damage desired grasses and plants. Again in this attempt, there was the specific control of a particular grass or weed, but the wide spectrum of control of weeds and grasses was not provided by such combination.

Now, we have found that by adding methane arsonic acid or salts thereof and cacodylic acid or salts thereof in a certain proportion that a synergistic effect is provided which results in the control of a wide spectrum of weeds and grasses.

The proportion of the individual components which when applied in combination provide the synergistic effect has been found to be between 1 and 2 pounds of cacodylic acid active equivalent and from about 2 to 4 pounds of monosodium acid methanearsonate active equivalent to be applied in a suitable carrier such as water to broadleaf weeds and grasses.

It has been found that this combination in this proportion provides control of an unusually wide range of broadleaf weeds and grasses, whereas the individual components of cacodylic acid and monosodium acid methanearsonate would not provide such a wide range of control of weeds and grasses. Moreover, it was found that when cacodylic acid and monosodium acid methanearsonate (MSMA) were mixed at proportions outside the range of 1 to 2 pounds of cacodylic acid and 2 to 4 pounds of MSMA, the same results were not obtained. That is, when more or less cacodylic acid is added than in this synergistic range, i.e. 1 to 2 pounds, as wide range of control of weed and grass growth was not obtained.

The preferred amounts per gallon of solution is about 1.25 parts by weight of cacodylic acid equivalent to about 3 parts by weight of methane arsonic acid equivalent. With this herbicide combination, it is possible to control the growth of broadleaf weeds and grasses such as Pigweed, Ivyleaf Morning Glory, Johnsongrass, Japanese Millet, and the like. The degree of control of the growth of certain weeds and grasses sprayed with various proportions of cacodylic acid and MSMA is given in TABLE I below. To the combinations, a surfactant has been added which amounts to about 0.25% by volume. The results are shown by the phytotoxicity of various combinations of cacodylic acid and MSMA to the various plant species. The phytotoxicity is indicated by a rating system where "0" is equal to no damage to weeds and grasses. The various combinations were applied in an aqueous spray at a volume of 50 gallons per acre to rapidly growing irrigated vegetation consisting of two broadleafed weeds, i.e. Ivyleaf Morning Glory and Pigweed, and two grasses, i.e. Japanese Millet and Johnsongrass.

TABLE 1

| Treatment/Acre | | Phytotoxicity Rating | | | |
|---|---|---|---|---|---|
| Pounds of Cacodylic Acid | Pounds of MSMA | Japanese Millet | Pigweed | Ivyleaf Morning Glory | Johnsongrass |
| 0 | 2 | 1.2 | 1.6 | 2.3 | 7.0 |
| 0 | 4 | 1.6 | 8.5 | 5.6 | 9.6 |
| 0 | 6 | 2.0 | 9.3 | 7.1 | 10.0 |
| 1.25 | 0 | 1.5 | 4.5 | 5.16 | 4.8 |
| 1.25 | 2 | 2.0 | 8.8 | 8.3 | 8.6 |
| 1.25 | 4 | 2.6 | 9.3 | 9.0 | 9.6 |
| 1.25 | 6 | 2.6 | 9.6 | 9.0 | 9.6 |
| 2.5 | 0 | 2.0 | 8.5 | 8.5 | 4.0 |
| 2.5 | 2 | 2.0 | 9.5 | 9.6 | 8.3 |
| 2.5 | 4 | 2.3 | 9.8 | 10.0 | 9.6 |
| 2.5 | 6 | 3.3 | 10.0 | 9.8 | 9.5 |
| 3.75 | 0 | 2.0 | 7.3 | 9.16 | 4.0 |
| 3.75 | 2 | 2.3 | 9.3 | 9.6 | 8.8 |
| 3.75 | 4 | 3.3 | 10.0 | 10.0 | 9.8 |
| 3.75 | 6 | 3.3 | 9.8 | 10.0 | 10.0 |

As shown in TABLE I, whether 2.0 or 4.0 pounds of MSMA is combined with 1.25 pounds of cacodylic acid, the activity on the broadleaf weeds is increased compared to either MSMA or cacodylic acid applied individually at these rates. The phytotoxicity on grasses, especially Johnsongrass, is also increased when this combination of MSMA and cacodylic acid are used compared to cacodylic acid applied alone. All the ratings in Table I are based on an average of three replications. It is noted that this type of combination of MSMA and cacodylic acid may be useful for controlling weeds and grasses in orchards, noncrop areas, prior to planting field crops, or anywhere cacodylic acid alone could be used.

As indicated above, cacodylic acid may be used in combination with other herbicides and effectively control particular weeds and grasses. In the following Table II, is given the phytotoxicity ratings of different herbicide combinations with cacodylic acid, and of individual herbicides. The phytotoxicity rating is given to indicate the effect thereof thirteen days after application of the spray solution at 40 psi pressure and at a volume of 40 gallons per acre.

TABLE II

| Treatments in pounds per acre | John-son-grass | Pig-weed | Ivyleaf Morning glory | Japanese Millet |
|---|---|---|---|---|
| 1.25 lbs Cacodylic acid 0.125 lbs Clobber | 1.0 | 4.0 | 3.0 | .12 |
| 1.25 lbs Cacodylic acid 0.25 lbs Clobber | 0 | 9.0 | 9.7 | .25 |
| 2.5 lbs Cacodylic acid 0.125 lbs Clobber | 3.5 | 9.7 | 10.0 | 3.5 |
| 1.25 lbs Cacodylic acid 0.125 lbs Karmex | 0.5 | 4.0 | 9.0 | 0.5 |
| 1.25 lbs Cacodylic acid 0.25 lbs Karmex | 0.75 | 10.0 | 9.0 | .25 |
| 2.5 lbs Cacodylic acid 0.125 lbs Karmex | 3.0 | 6.0 | 10.0 | 1.5 |
| 1.25 lbs Cacodylic acid 0.125 lbs Hyvar X | 0.5 | 3.5 | 7.5 | 0.5 |
| 2.5 lbs Cacodylic acid 0.125 lbs Hyvar X | 2.5 | 9.25 | 10 | .25 |
| 2.5 lbs Cacodylic acid 0.25 lbs Hyvar X | 2.0 | 8.7 | 10 | 1.2 |
| 1.25 lbs Cacodylic acid 0.25 lbs Atrazine | 2.1 | 7.2 | 5.0 | 0.5 |
| 1.25 lbs Cacodylic acid 0.5 lbs Atrazine | 0.5 | 5.7 | 9.0 | 0.5 |
| 2.5 lbs Cacodylic acid 0.25 lbs Atrazine | 4.5 | 9.0 | 9.5 | .75 |
| 1.25 lbs Cacodylic acid 2.0 lbs MSMA | 6.5 | 9.25 | 9.25 | 2.0 |
| 1.25 lbs Cacodylic acid 4.0 lbs MSMA | 9.7 | 9.5 | 10 | 4.0 |
| 2.5 lbs Cacodylic acid 2.0 lbs MSMA | 8.5 | 9.7 | 10 | 3 |
| 2.5 lbs Cacodylic acid 4.0 lbs MSMA | 9.7 | 9.5 | 10 | 3 |
| 1.25 lbs Cacodylic acid 1.5 lbs maleic hydrazide | .75 | 6.25 | 4.5 | 0.25 |
| 2.5 lbs Cacodylic acid 1.5 lbs maleic hydrazide | 1.5 | 8.25 | 9.0 | 1.25 |
| 2.5 lbs Cacodylic acid 3.0 lbs maleic hydrazide | 3.0 | 9.0 | 9.5 | 1.0 |
| 1.25 lbs Cacodylic acid 0.25 lbs 2,4-D | 0.5 | 7.0 | 9.5 | 0.5 |
| 2.5 lbs Cacodylic acid 0.25 lbs 2,4-D | 1.7 | 9.5 | 10.0 | 0.5 |
| 1.25 lbs Cacodylic acid | 1.0 | 4.5 | 6.0 | 0.5 |
| 2.5 lbs Cacodylic acid | 2.5 | 5.0 | 9.0 | 0.5 |
| 0.125 lbs Clobber | 0 | .12 | .12 | 0 |
| 0.25 lbs Clobber | 0 | 1.0 | 2.0 | 0 |
| 0.5 lbs Clobber | 0 | 4.7 | 5.5 | 0 |
| 0.125 lbs Karmex | 0 | 2.0 | 3.0 | 0 |
| 0.25 lbs Karmex | .12 | 10.0 | 9.5 | 0 |
| 0.125 lbs Hyvar X | 0 | .5 | 2.5 | 0 |
| 0.25 lbs Hyvar X | 0 | 2.0 | 4 | 0 |
| 0.5 lbs Hyvar X | 0 | 7.0 | 8.5 | 0 |
| 0.25 lbs Atrazine | 0 | .25 | .25 | 0 |
| 0.5 lbs Atrazine | 0 | 3.5 | 3.5 | 0 |
| 2.0 lbs MSMA | 8.5 | 3.5 | 2.5 | 3.0 |
| 4.0 lbs MSMA | 10.0 | 9.0 | 7.7 | 6.0 |
| 1.5 lbs maleic hydrazide | 0 | 0 | 0 | 0 |
| 3.0 lbs maleic hydrazide | 0 | 0 | 0 | 0 |
| 0.25 lbs 2,4-D | 0 | 8.0 | 10.0 | 0 |

As shown in Table 2, most of the herbicides at the rates used either in combination with cacodylic acid or applied alone were very weak on grasses. The exception was MSMA which when applied either alone or in combination with the cacodylic acid. The results recorded in Table II further illustrate the significance of the combination of cacodylic acid and MSMA for the control of a broad spectrum of broadleaf weeds and grasses.

What is claimed is:

1. A method of controlling the growth of pigweed and ivyleaf morning glory which comprises applying to an area containing said plants an aqueous solution of a first herbicide selected from the group consisting of cacodylic acid and its salts, a second herbicide selected from the group consisting of methane arsonic acid and its salts, and a surfactant, the first herbicide being applied at a rate of 1 to 2 pounds of cacodylic acid equivalent per acre, the second herbicide being applied at a rate of 2 to 4 pounds of methane arsonic acid equivalent per acre, and the solution containing no more than about 0.25% by volume of surfactant.

* * * * *